United States Patent
Bakos et al.

(10) Patent No.: US 7,309,344 B2
(45) Date of Patent: Dec. 18, 2007

(54) TRANSPARENT DILATOR DEVICE AND METHOD OF USE

(75) Inventors: Gregory J. Bakos, Mason, OH (US); Kurt R. Bally, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 342 days.

(21) Appl. No.: 10/324,597

(22) Filed: Dec. 20, 2002

(65) Prior Publication Data

US 2004/0122462 A1    Jun. 24, 2004

(51) Int. Cl.
*A61M 29/00* (2006.01)
(52) U.S. Cl. .................................................. 606/190
(58) Field of Classification Search ............... 606/191; 600/114, 117
See application file for complete search history.

(56) References Cited

U.S. PATENT DOCUMENTS

| | | | |
|---|---|---|---|
| 719,487 A | 2/1903 | Minor | |
| 3,169,527 A * | 2/1965 | Sheridan | 604/172 |
| 4,195,624 A | 4/1980 | Douglas | |
| 4,449,532 A * | 5/1984 | Storz | 606/191 |
| 4,571,239 A | 2/1986 | Heyman | |
| 4,646,722 A | 3/1987 | Silverstein et al. | |
| 4,726,373 A | 2/1988 | Greengrass | |
| 4,773,394 A | 9/1988 | Reichstein et al. | |
| 4,825,861 A | 5/1989 | Koss | |
| 4,832,691 A | 5/1989 | Witzel | |
| 4,862,891 A * | 9/1989 | Smith | 606/191 |
| 4,871,358 A * | 10/1989 | Gold | 604/271 |
| 5,006,106 A | 4/1991 | Angelchik | |
| 5,188,596 A * | 2/1993 | Condon et al. | 604/103.1 |
| 5,366,471 A | 11/1994 | Jones et al. | |
| 5,370,625 A * | 12/1994 | Shichman | 604/174 |
| 5,603,991 A * | 2/1997 | Kupiecki et al. | 427/508 |
| 5,624,432 A | 4/1997 | Angelchik | |
| 5,718,666 A | 2/1998 | Alarcon | |
| 5,733,241 A * | 3/1998 | King | 600/114 |

(Continued)

FOREIGN PATENT DOCUMENTS

CH    661 665 A5    8/1987

(Continued)

OTHER PUBLICATIONS

Buess G, Thon J, Hutterer F. A Multiple-diameter Bougie fitted over a small-caliber fiberscope *Endoscopy* 15 (1983) 53-54.

(Continued)

*Primary Examiner*—Anhtuan T. Nguyen
*Assistant Examiner*—Elizabeth Houston (57) ABSTRACT

A medical device for use with an endoscope is provided. The medical device can include a tube with a first channel for receiving the endoscope. A transparent segment can extend from the distal end of the tube, and the transparent segment can have a first outer diameter sized for providing dilation of a portion of a body lumen. The medical device can also include a tapered tip attached to the distal end of the transparent segment that narrows from the first outer diameter to a distal terminating end. The endoscope is used to view the body lumen through the medical device while in use to dilate a stricture under direct visualization.

10 Claims, 6 Drawing Sheets

U.S. PATENT DOCUMENTS

| | | | |
|---|---|---|---|
| 5,766,202 A | | 6/1998 | Jones et al. |
| 5,968,065 A | | 10/1999 | Chin |
| 6,010,520 A | * | 1/2000 | Pattison ...................... 606/191 |
| 6,033,361 A | * | 3/2000 | Co et al. ..................... 600/210 |
| 6,142,931 A | | 11/2000 | Kaji |
| 6,238,404 B1 | * | 5/2001 | Hidalgo et al. ............. 606/148 |
| 6,334,863 B1 | | 1/2002 | Srinivasan |
| 6,527,704 B1 | * | 3/2003 | Chang et al. ................ 600/112 |
| 6,652,442 B2 | * | 11/2003 | Gatto ............................. 600/3 |
| 6,726,659 B1 | * | 4/2004 | Stocking et al. ........ 604/164.09 |
| 6,743,218 B2 | * | 6/2004 | Maginot et al. ............. 604/510 |
| 6,796,976 B1 | * | 9/2004 | Chin et al. ................... 604/523 |
| 2003/0153874 A1 | * | 8/2003 | Tal ............................ 604/164.1 |
| 2004/0087991 A1 | * | 5/2004 | Woo ............................ 606/185 |
| 2004/0122462 A1 | | 6/2004 | Bakos et al. |
| 2005/0049570 A1 | * | 3/2005 | Chin et al. ................... 604/500 |
| 2005/0070949 A1 | | 3/2005 | Bakos et al. |

FOREIGN PATENT DOCUMENTS

| | | |
|---|---|---|
| CH | 661665 A5 | 8/1987 |
| EP | 1430926 A2 | 6/2004 |
| GB | 2023009 A | 12/1979 |
| WO | WO 84/04462 A1 | 11/1984 |
| WO | WO 90/00914 * | 2/1990 |
| WO | WO 90/00914 A | 2/1990 |
| WO | WO 98/47422 A2 | 10/1998 |
| WO | WO 90/00914 A | 12/2000 |
| WO | WO 01/12255 * | 2/2001 |
| WO | WO 01/12255 A | 2/2001 |
| WO | WO 01/12255 A1 | 2/2001 |

OTHER PUBLICATIONS

Buess G, Thon J. Eitenmuller J, Schellong H, Hildebrand E, Hutterer F. The endoscopic Multiple-diameter bougie-Clinical results after one year of application, *Endoscopy* 15(6) (1983) 337-341.

Chung RSK, Safaie Shirazi S, Denbesten L. Dilation of esophageal strictures: A new technique controlled by fiberoptic endoscopy. *Archives of Surgery* vol. 111 (Jul. 19976) 795-8.

Cox JGC, Dakkak M, Buckton GK, Bennett Jr. Dilators for esophageal stricture—a description of an ew bougie and a comparison of current instruments. *Gastrointestinal Endoscopy* vol. 35 No. 6 (1989) vol. 35 No. 6 (1989) 551-4.

Spees EK. A simplified esophageal dilator. *Military Medicine* vol. 146 (Apr. 1981) 290.

Lilly JO. McCaffery. Esophageal dilator. *Military Medicine* vol. 146 No. 12 (Dec. 1971) 1137-40.

Chinese Patent Office office action issued Mar. 4, 2005 004 for corresponding Chinese Patent Application No. 200310109792.8.

EPO Search Report dated Oct. 13, 2004 for corresponding European Patent Application No. EP 03 25 8098.

International Search Report dated Dec. 21, 2005 for corresponding application EP 05 52 6423.4.

EPO Search Report dated Dec. 13, 2005 for corresponding patent application, European Patent Application No. EP 05 25 6423.

* cited by examiner

TRANSPARENT DILATOR DEVICE AND METHOD OF USE

FIELD OF THE INVENTION

The present invention relates to a transparent dilator device for use in a lumen of a patient's body.

BACKGROUND

Constriction of natural body lumens, such as those of the human gastrointestinal tract, can occur in numerous ways. Some strictures are caused by muscular spasm, others by disease, and others by injury. Regardless of the cause, the typical method of treatment is to physically dilate the region using a medical device designed for that purpose.

Several types of devices are used for dilation. One generally established type is a bougie. Bougie tubes may be in the form of a mercury- or tungsten-filled tube with a tapered end that gradually opens the strictured esophagus as it is pushed past the treatment site. These devices come in a series of increasing sizes, each tube having a single effective dilating diameter, generally between 10 and 60 French. (French is a measure of circumference based on the diameter in millimeters, mm.) The bougie is typically introduced blindly after the physician has judged the proper beginning size with an endoscope. Some physicians follow a rule of thumb not to dilate a stricture more than three successive French sizes (3 mm) in a single session. If the lumen has not satisfactorily been opened after three sizes, the patient returns at a later time for another treatment session.

Another type of device is a wire-guided dilator. These devices are passed into the patient over a guidewire that has been pre-fed along a lumen of the gastrointestinal tract. The guidewire keeps the tip of the device in the lumen while it is being passed, to avoid perforating through the wall of the lumen. These devices have a single outer dilating diameter and typically have a radiopaque component so that they are visible under fluoroscopy. The following patent documents disclose various devices in the art: U.S. Pat. No. 5,366,471; U.S. Pat. No. 6,334,863; U.S. Pat. No. 5,766,202; and GB 2023009A.

A third type of dilating device is a balloon. Balloon dilators may be comprised of polyethylene, and may be introduced through the working channel of an endoscope. The physician views the proximal end of a stricture site with an endoscope and introduces the deflated balloon into the narrowed area. The balloon is then inflated with saline or other fluid to effectively open the stricture site pneumatically. Balloons provide the advantages of multiple dilator diameters with a single intubation, passage through the working channel of an endoscope, and visualization of a stricture site from the proximal end.

Other devices such as double tapered bougies, pneumatic bougies, illuminating bougies, solid dilator devices attached to the distal end of an endoscope, and variable stiffness dilators have been previously described in the art. The following patent documents disclose various types of devices in the art: U.S. Pat. No. 6,010,520; U.S. Pat. No. 4,832,691; U.S. Pat. No. 5,624,432; U.S. Pat. No. 5,718,666; WO 98/47422.

SUMMARY OF THE INVENTION

Applicants have recognized the need for a relatively low cost dilator (disposable or non-disposable) which is relatively easy and convenient to use, and which allows the physician to directly visualize the stricture being dilated. In one embodiment, the present invention provides a medical device for use in dilating a body lumen. The medical device comprises at least one generally transparent segment, and a channel associated with the transparent segment for receiving a visualization device. The transparent segment includes at least one outer surface having a diameter sized for providing dilation. In one embodiment, the device can comprise a plurality of transparent sections, each section having an outer surface portion with a different diameter sized for sequential dilation of a stricture. The medical device can include at least one marking associated with the transparent segment for indicating the position and/or value of a dilation diameter.

The present invention also provides a method for dilating a portion of a body lumen. In one embodiment, the method can comprise the steps of: providing a medical device having at least one outer surface portion sized for providing dilation of a body lumen; inserting said outer surface portion into said lumen; advancing said outer surface portion in said lumen to dilate said lumen; and viewing dilation of said lumen through said outer surface portion of said medical device, such as by viewing the body lumen with a visualization device positioned within a channel in the medical device. The step of viewing dilation can comprise viewing the lumen through a transparent segment of device, wherein the transparent segment includes multiple outer diameters sized and arranged for sequential dilation.

BRIEF DESCRIPTION OF THE DRAWINGS

While the novel features of the invention are set forth with particularity in the appended claims, the invention in all its embodiments may be more fully understood with reference to the following description and accompanying drawings.

FIGS. 7A-7D illustrate steps which can be performed in using dilator 18 with an endoscope 50. FIG. 7D)

is a sectional view of dilator 18 from FIG. 5 and field of view 52 of endoscope 50 positioned at third viewpoint 55 dilating to third outer diameter D3.

DETAILED DESCRIPTION OF THE INVENTION

The present invention relates to the field of medicine, specifically to surgery, urology, or gastroenterology, in which a physician intends to alter the size of a constricted body lumen in a patient, or otherwise temporarily or permanently enlarge a portion of a body lumen. By way of example, the present invention is illustrated and described for application to an esophageal stricture of a human patient. However, the present invention is applicable for use in other natural lumens of human patients, including the urinary tract, biliary tract, lower gastrointestinal tract, or bronchus; and the present invention may also be used in other animals (e.g. for veterinary medicine), including mammals other than humans.

Figure 1:
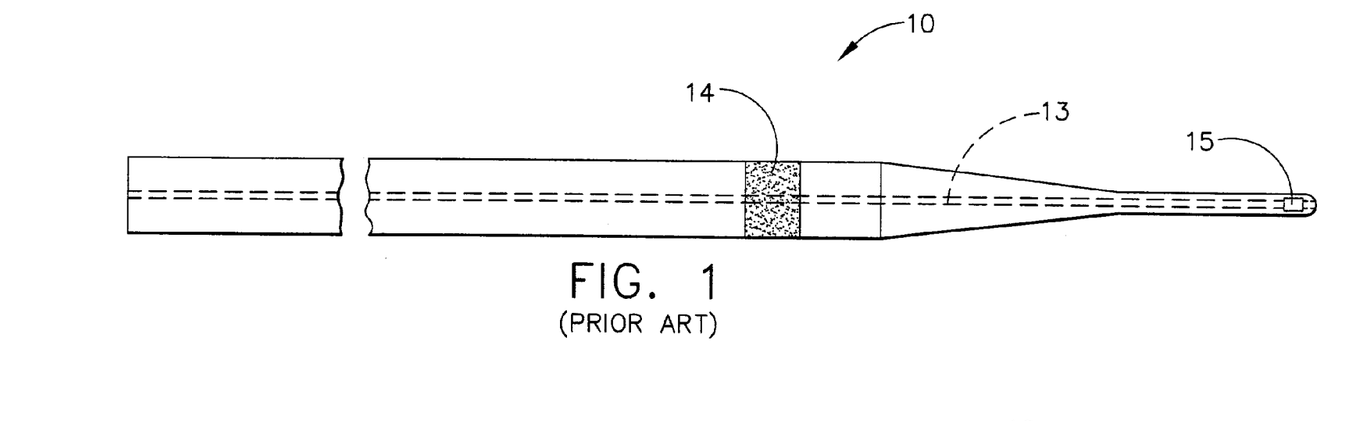
FIG. 1 is a side view of wire-guided dilator 10, described in prior art, including a guidewire channel 13, a first radiopaque marker 14, and a second radiopaque marker 15.

FIG. 1 shows a wire-guided dilator 10 described in prior art, including a guidewire channel 13, a first radiopaque marker 14, and a second radiopaque marker 15. Guidewire channel 13 allows wire-guided dilator 10 to be passed over a previously placed guidewire along the lumen of a patient. First radiopaque marker 14 and second radiopaque marker 15 are detectable under fluoroscopy to determine the position of wire-guided dilator 10 relative to a strictured area. This provides confirmation to the physician of dilation to the full diameter of the device. The fluoroscopy procedure can be costly and can expose the physician and patient to radiation.

Figure 2:
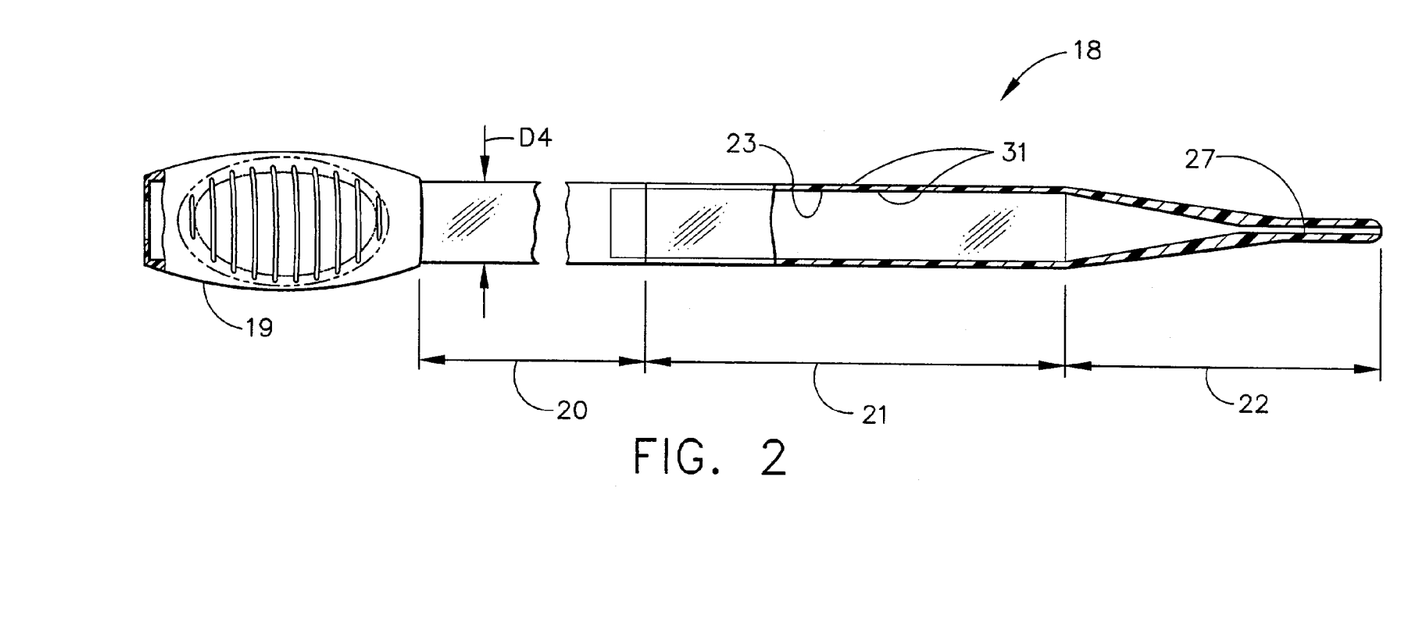
FIG. 2 is a side view of a first embodiment of the present invention, a dilator 18 which includes a handle 19, a tube 20, a transparent segment 21, and a tapered tip 22.

FIG. 2 shows a dilator 18 of the present invention, including a handle 19 at the device's proximal end, a tube 20, a transparent segment 21, and a tapered tip 22 at its distal end. Handle 19 of FIG. 2 includes a longitudinal channel for receiving an endoscope 50 (see FIG. 3). Handle 19 provides the physician a location to grip dilator 18 and may be made from an elastic material, such as silicone. In one embodiment, the proximal portion of handle 19 can have an opening (such as an opening in a flexible, elastic seal or boot made of silicone or a suitable flexible elastic polymeric material), the hole being slightly smaller than the diameter of the endoscope. Such an arrangement can provide frictional engagement of the handle 19 with the endoscope 50 due to the drag force encountered in passing the endoscope through the opening. This feature allows the physician to hold either endoscope 50 or tube 20 in a one-handed fashion to position both the endoscope and the dilator 18 with direct visualization of a body lumen 60 (FIG. 3) during introduction or advancement of the device.

Tube 20 shown in FIG. 2 may be made of a flexible polymer, examples of which include polyvinyl chloride (PVC), thermoplastic elastomer (TPE), polyurethane, or silicone. In one embodiment, tube 20 is made of a transparent flexible polymer, but it may also be made from an opaque material. A suitable transparent material from which tube 20 can be manufactured is available as 2222RX-70 Clear 000X from Alpha-Gary Corporation (Leominster, Mass.). Commercially available clear flexible PVC tubing such as Kuri Tec K050 0810 from Kuriyama of America Inc. (Elk Grove Village, Ill.) may also be used for tube 20.

Figure 3:
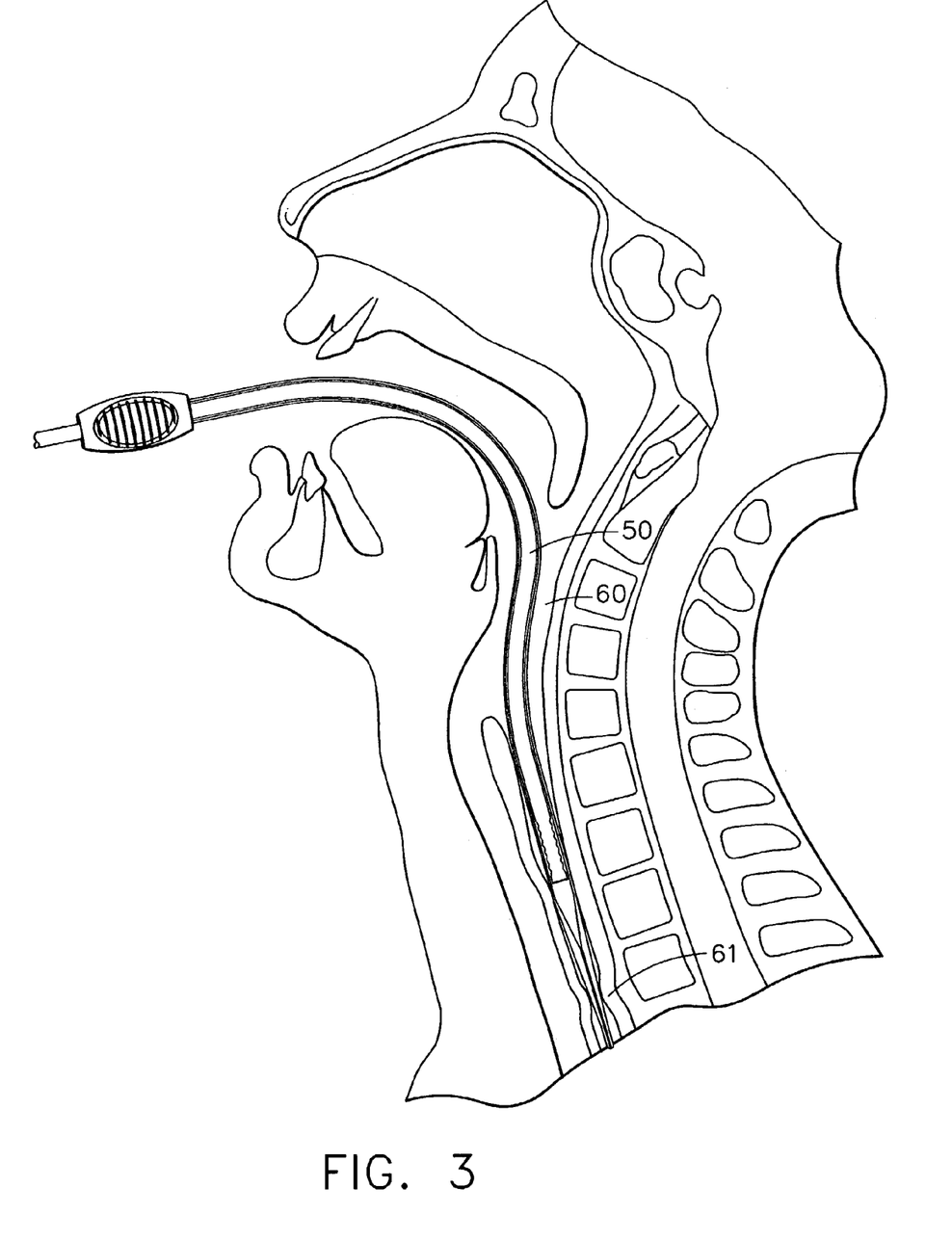
FIG. 3 is a sectional view of dilator 18 from FIG. 2 with an endoscope 50 inside a body lumen 60, proximal to a stricture 61.

First channel 23 of FIG. 2 is appropriately sized to receive endoscope 50 (see FIG. 3). Various endoscopes of varying types and sizes may be used inside the present invention, including, but not limited to, bronchoscopes, colonoscopes, cystoscopes, and gastroscopes. Endoscope 50 may comprise a fiberscope or a videoscope, and may employ a CMOS (Complimentary Metallic Oxide Semiconductor) chip, a miniature camera, or other visualization device. In one embodiment, first channel 23 may be about 2 mm greater in diameter than the diameter of endoscope 50 used in the procedure so that relative motion between endoscope 50 and dilator 18 can occur smoothly under physician control. By way of example, a 9.5 mm diameter gastroscope could be inserted into an 11.5 mm diameter first channel 23 of dilator 18 to dilate an esophageal stricture. However, dilator 18 can be sized and configured to accommodate other endoscopes. In various other embodiments, first channel 23 may have a diameter in the range of, but not limited to, about 3 mm to about 15 mm.

Fourth outer diameter D4 of FIG. 2 can be made as small as feasible for reason of patient tolerance during the procedure. Fourth outer diameter D4 may be the same as the largest diameter of transparent segment 21, or alternatively, D4 may be less than the largest diameter in transparent segment 21. The dimensions of first channel 23 and fourth outer diameter D4 determine the wall thickness of tube 20. This wall thickness should provide adequate axial stiffness to advance transparent segment 21 of dilator 18 past stricture 61 without kinking, when used in conjunction with endoscope 50. The presence of endoscope 50 inside tube 20 during advancement adds to the stiffness of dilator 18, and greatly reduces the likelihood of kinking or folding tube 20 during use. When tube 20 is made from a flexible polymer such as a flexible PVC material, wall thickness including a range from about 1 mm to about 4 mm may be used. If a portion of transparent segment 21 is made from a relatively more rigid material, a wall thickness of 1 mm or less may be used.

The length of tube 20 in FIG. 2 should be appropriately sized to comfortably reach the targeted area within the body while handle 19 remains outside the body for physician control. A low coefficient of friction on tube 20 allows easy sliding along the surface of body lumen 60. And, because the physician can reposition endoscope 50 within tube 20 to get a different view, easy sliding of endoscope 50 within tube 20 may also be desired. A suitable lubricant or low friction material (wet or dry) can be employed. For instance, a lubricating gel may be used to lower the coefficient of friction between tube 20 and body lumen 60, and between endoscope 50 and tube 20. Likewise, a suitable lubricant or other low friction material (such as a coating 31 shown in FIG. 4) could be applied to the inner or outer surfaces (or both) of tube 20 or transparent segment 21 (or both) to facilitate sliding of endoscope 50 within tube 20 and also sliding of tube 20 within body lumen 60.

FIG. 3 shows the dilator 18 being used in body lumen 60 to dilate a stricture 61. Dilator 18 dilates stricture 61 in body lumen 60 under direct visualization by endoscope 50 positioned inside the device, allowing the physician to see along the entire length of stricture 61 from the inside out. The invention replaces the current methods of dilating body lumen 60 without direct visualization and improves on current methods of dilating with balloons and other devices that allow visualization from only the proximal side of stricture 61 during the procedure. By way of example, this illustration shows the invention used to dilate an esophageal stricture, but it could be used to dilate constrictions in other body lumens.

Figure 4:
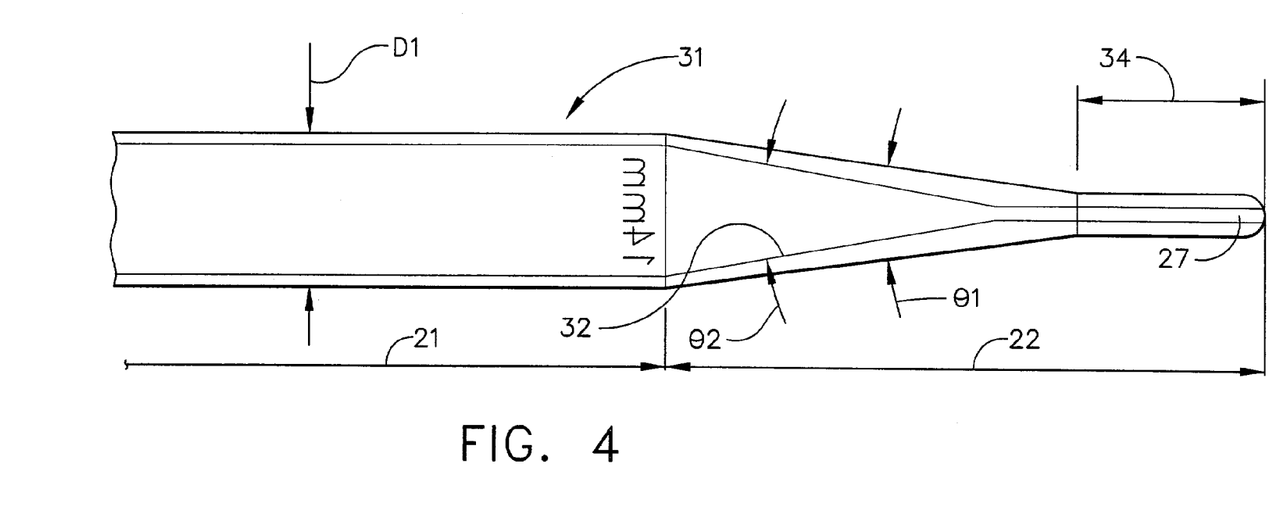
FIG. 4 is a detailed view of transparent segment 21 and tapered tip 22 shown in FIG. 2, including a first outer diameter D1, a conical inner contour 32 inside tapered tip 22, an exterior taper angle theta1, and a narrow leading edge 34.
Figure 5:
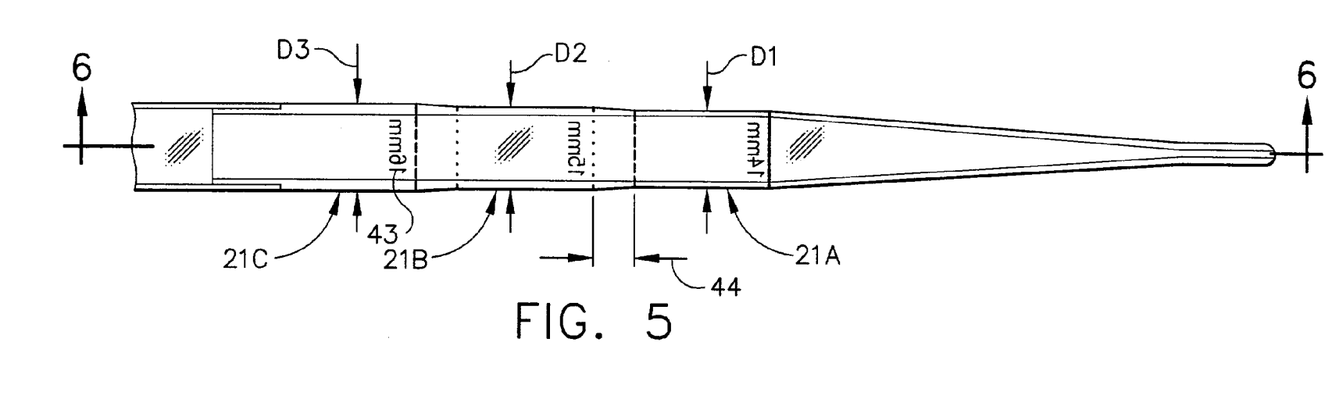
FIG. 5 shows a detail view of a preferred embodiment of transparent segment 21, including a second outer diameter D2, a third outer diameter D3, a plurality of markings 43, and at least one transition 44.

Transparent segment 21 shown in FIG. 4 and in FIG. 5 is a transparent portion of the device through which a physician views the stricture 61 during dilation of stricture 61. Transparent segment 21 extends from the distal portion of tube 20 and may be made of a transparent material, including clear PVC, TPE, polyurethane, glass, or polycarbonate. Attachment means for attaching transparent segment 21 to tube 20 may include a flange with adhesive, a plurality of mechanical ribs, a plurality of screw-type threads, or other combinations of geometric projections and adhesives. Tube 20 and transparent segment 21 may also be formed as a single, unitary piece, such as by forming tube 20 and transparent segment 21 together by molding or casting. Rigid segments may also be incorporated into transparent segment 21, especially in instances where wall thickness is about 1 mm or less. Such rigid segments could be overmolded in place or fixed by adhesive in a desired location. In one embodiment, first channel 23 (FIG. 2) extends into transparent segment 21 so that endoscope 50 may be advanced within transparent segment 21.

The transparency of transparent segment 21 allows direct visualization of tissue outside the device from endoscope 50 located within the device. Therefore, it can be desirable to minimize distortion or obstruction of view through transparent segment 21. Suitable transparency of transparent segment 21 can be accomplished by controlling material selection and molding finish. The material from which transparent segment 21 is constructed should be clear, and the mold used should be polished so that the molded part has a smooth outer surface. Transparent segment 21 may include markings 43 (FIG. 5) such as one or more markings 43 indicating the outside diameter of transparent segment 21 at the longitudinal position of the particular marking. Anatomical landmarks, color variations, tissue differences, foreign bodies, and any markings 43 (FIG. 5), and other items of interest should be recognizable when viewed with endoscope 50 disposed within transparent segment 21. An appropriate material for transparent segment 21 can have a haze value of about 5% or less, and have a light transmission property of about 80% or greater. Haze value is a material property, expressed in percent, describing the amount of "cloudiness" in a material caused by particulate impurities, molecular structure, or degree of crystallinity, resulting in scattering of light and apparent cloudiness. Light transmission is a material property indicating the percentage of incident light that passes through an object. In addition to using transparent material to form segment 21, a mold used to create segment 21 can be highly polished to create a smooth surface that does not distort the view seen through endoscope 50 when the viewing device of endoscope is disposed inside segment 21 to view lumen tissue outside of segment 21.

Having a low coefficient of friction of transparent segment 21 allows the device to slide freely inside body lumen 60, especially during dilation of stricture 61. Lubricating gel, such as K-Y brand lubricating jelly available from Johnson and Johnson can be used to lower the coefficient of friction during use. In one embodiment, a coating 31 (FIG. 2) can be disposed on one or both of the inner and outer surfaces of the transparent segment 21, in which coating 31 is transparent and has a lower coefficient of friction when hydrated than when dry. One example of coating 31 is a hydrogel material made by the interaction of poly-vinylpyrrolidone with one or more isocyanate prepolymers. A coating such as Hydromer® Lubricious Medical Coatings by Hydromer Inc. (Somerville, N.J.) can be used for coating 31. Such a coating can reduce the drag force along the axis of a lumen during dilation, creating a more efficient device when compared to existing dilators.

FIG. 4 shows a section view of dilator 18 including a first outer diameter D1 and a tapered tip 22. Tapered tip 22 may be made of a flexible polymer that is pliable compared to body tissue and may be attached to the distal end of transparent segment 21. In one embodiment, tapered tip 22 can be made with the same material as transparent segment 21, if transparent segment 21 is made of a flexible polymer. In one embodiment, a biomedical grade of clear flexible PVC having a hardness value of about 60 to 80 on the Shore A scale can be used to form tapered tip 22 and transparent segment 21. For example, a clear flexible PVC material such as XV-3450 from PolyOne Corp. (Avon Lake, Ohio) could be used to mold both transparent segment 21 and tapered tip 22 as a single part. Another material from which tip 22 and segment 21 may be formed is material designated 2222RX-70 Clear 000X from Alpha-Gary Corp (Leominster, Mass.), which material can be gamma stable to allow gamma radiation to be used for sterilization. Other suitable materials such as TPE or polyurethane can also be used.

Tapered tip 22 facilitates intubation into body lumen 60 by gradually tapering from a first outer diameter D1 to a narrow leading segment 34 with an exterior taper angle theta1, as shown in FIG. 4. In one embodiment, tapered tip 22 includes a second channel 27 in communication with a conical inner contour 32 and first channel 23 so that the device can be threaded over a guidewire. Second channel 27 can be sized appropriately for a guidewire, including diameters in the range from about 0.5 mm to about 1.5 mm. Exterior taper angle theta1 can be selected to provide a desired amount of radial force transmitted against stricture 61 for a given level of axial force (force parallel to length of the dilator 18) applied by the physician. Generally, a low value of exterior taper angle provides an efficient, comfortable transmission of radial force against the stricture, with the trade-off that low values of exterior taper angle generally increase the length of the dilator 18 that must be inserted past the stricture. For instance and without limitation, the dilator can have an exterior taper angle theta1 in a range including about 3 degrees to about 15 degrees. In one embodiment, the taper angle can be between about 6.5 and about 7.5 degrees.

FIG. 4 shows conical inner contour 32 connecting first channel 23 to second channel 27 with an interior taper angle theta2. The connection has a conical shape to reduce the glare from endoscope 50 during use. Conical inner contour 32 also facilitates molding by allowing a central core pin to be tapered for ease of removal. In one embodiment, the value of interior taper angle theta2 is different from value of exterior taper angle theta1 to provide a varying wall thickness along the length of the device, so that radial strength can be tailored as needed along the length of the device. By way of example, the exterior taper angle theta1 can be about 7 degrees, and the interior taper angle theta2 can be about 6 degrees.

In FIG. 4, conical inner contour is shown initiating at the distal end of a segment with first outer diameter D1, but other initiation locations are possible. For example, if conical inner contour 32 initiates at a more proximal location (e.g. forward of the "14 mm" marking in FIG. 4), a thicker wall is created at the distal portion of a segment with first outer diameter D1, providing radial stiffness to that area while still allowing endoscope 50 to slide far enough to view out tapered tip 22 during insertion. Such an arrangement can help ensure adequate radial strength of in the portion of the device having inner diameter D1.

FIG. 5 depicts a preferred embodiment of transparent segment 21 comprised of a first transparent section 21A having a first outer diameter D1; a second transparent section 21B having a second outer diameter D2, and a third transparent section 21C having a third outer diameter D3, each pair of adjacent sections separated by a transition 44. The first, second and third sections can each be generally cylindrical. Transitions 44 provide a tapered (linear or curvilinear) transition in diameter from the outer diameter of one section to the outer diameter of the adjacent section. The transitions can have can have a hollow conical configuration, such as a conical shape generally the same as that of a truncated cone having a centrally located passageway. Alternatively, the dilator 18 can have diameters D1, D2, D3, and D4 on a single continuous outer surface portion which is tapered linearly or curvilinearly from D1 to D4.

FIG. 5 also shows plurality of markings 43 for the physician to select and position the desired dilating diameter in the area of stricture 61 during the procedure. Markings 43 provided to be visible through the optical device (e.g. camera, fiber optic cable, etc.) associated with the endoscope 50 and may have several uses, including delineating the boundaries of a single dilating diameter, or indicating the numeric value of a dilating diameter. Markings 43 may be molded into the part, applied with ink, etched on the device, or applied by any other suitable method. In one embodiment, numerical indications may be applied to the outer surface of transparent segment 21 in multiple locations, some of which are readable by endoscope 50 from inside the device (necessitating them to appear backwards from the exterior of the device, but appearing forward from inside the device), and some of which are readable from the exterior of the device (appear backward from endoscope 50 inside the device). In addition to markings comprising numerals or letters, other embodiments of plurality of markings 43 may include use of various other indicia, including without limitation one or more different colors, and/or use of different geometric shapes, such as to designate different sections or segments, or attributes of different portions of the device. For instance, a row or column of circles could be used to designate a first section, a pattern of circles and dashes could designate a second section, and a pattern of circles, dashes, and squares could designate a third section. Markings 43 can also be coated or otherwise treated with a substance to make them luminous or glow in reduced lighting.

Figure 6:
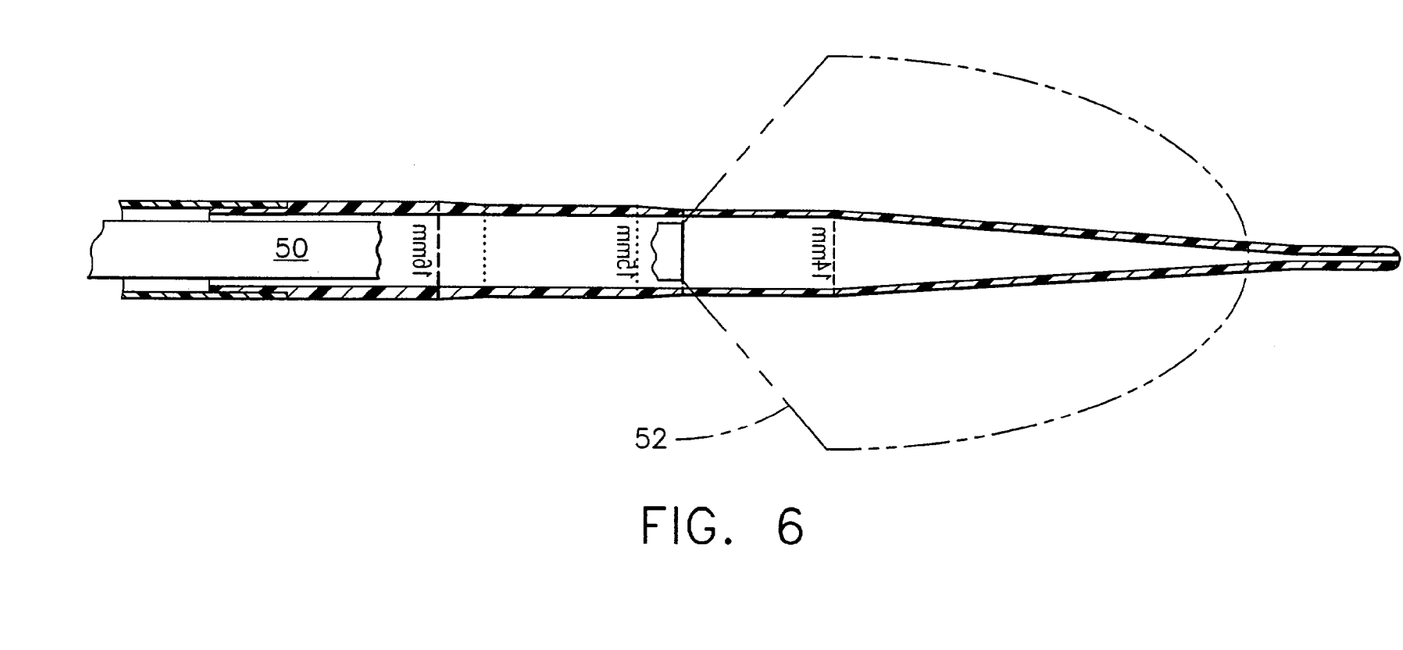
FIG. 6 shows endoscope 50 inside a cross section view of dilator 18 shown in FIG. 5, taken at line 6-6, including a field of view 52.

FIG. 6 shows a cross section of transparent segment 21 and tapered tip 22 of FIG. 5 taken at line 6-6 with endoscope 50 positioned inside. A field of view 52 is depicted to indicate the area in view by the physician. Because endoscope 50 is movable with respect to dilator 18, a change in the position of endoscope 50 allows the physician to see a different area of body lumen 60 within field of view 52.

Figure 7A:
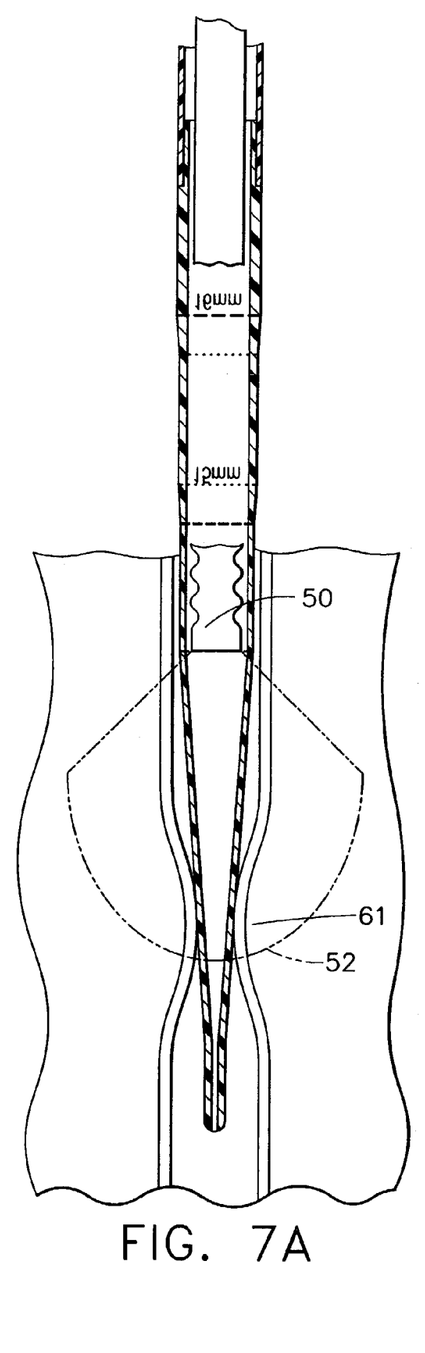
FIG. 7A) is a sectional view of dilator 18 from FIG. 5 and field of view 52 of endoscope 50 positioned for advancement into body lumen 60 to a stricture 61.

FIGS. 7A-7D show four possible steps a physician may use to dilate stricture 61 with dilator 18 and endoscope 50. FIG. 7A shows the relative positions of endoscope 50 and dilator 18 upon insertion into body lumen 60 to a location of stricture 61. In this position, field of view 52 is used to view body lumen 60 during insertion, and to view the proximal location of stricture 61.

Figure 7B:
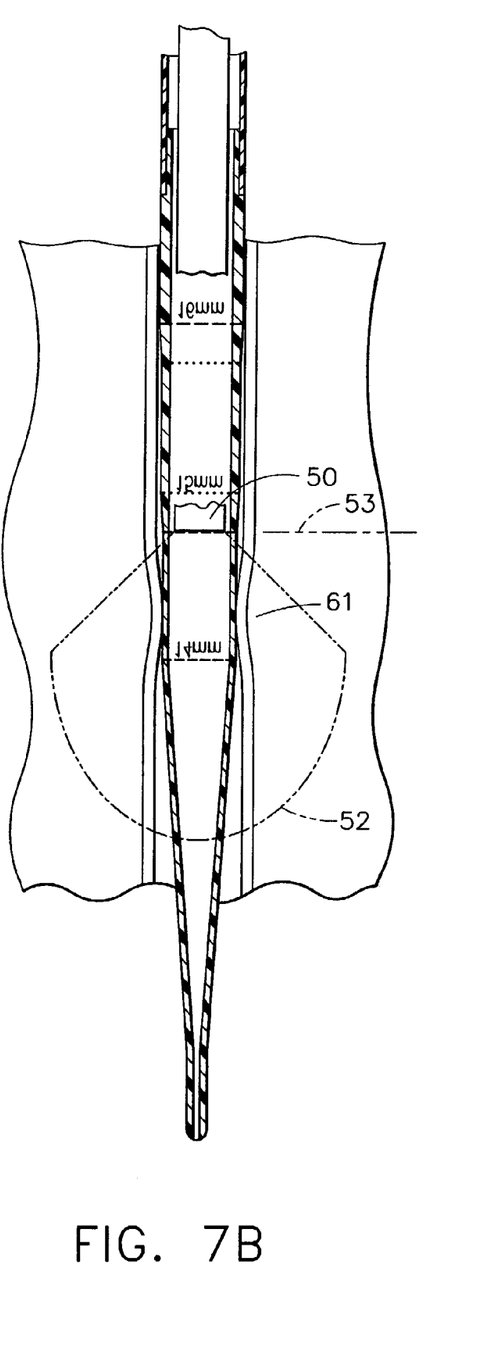
FIG. 7B) is a sectional view of dilator 18 from FIG. 5 and field of view 52 of endoscope 50 positioned at first viewpoint 53 dilating to first outer diameter D1.

FIG. 7B shows endoscope 50 at a first viewpoint 53 so field of view 52 includes first outer diameter D1. While viewing plurality of markings 43 for reference, dilator 18 is advanced into stricture 61 causing dilation to first outer diameter D1. Plurality of markings 43 may delineate the boundaries of diameter D1 and may also indicate its numerical value. In this manner, the physician has a visual indication through endoscope 50 of where to position dilator 18 with respect to stricture 61 for precise dilation to a desired diameter.

Figure 7C:
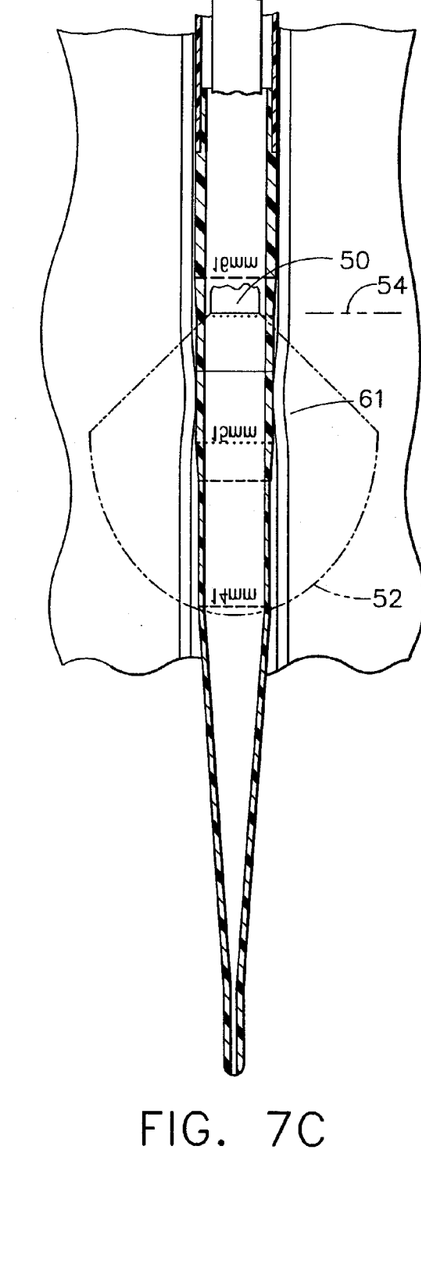
FIG. 7C) is a sectional view of dilator 18 from FIG. 5 and field of view 52 of endoscope 50 positioned at second viewpoint 54 dilating to second outer diameter D2.

FIG. 7C shows a next potential step to further dilate stricture 61 if desired by the physician. Endoscope 50 is placed at a second viewpoint 54 relative to dilator 18 so that field of view 52 includes second outer diameter D2. The medical device is further advanced into stricture 61 to further dilate to second outer diameter D2 while viewing another portion of plurality of markings 43 for reference.

Figure 7D:
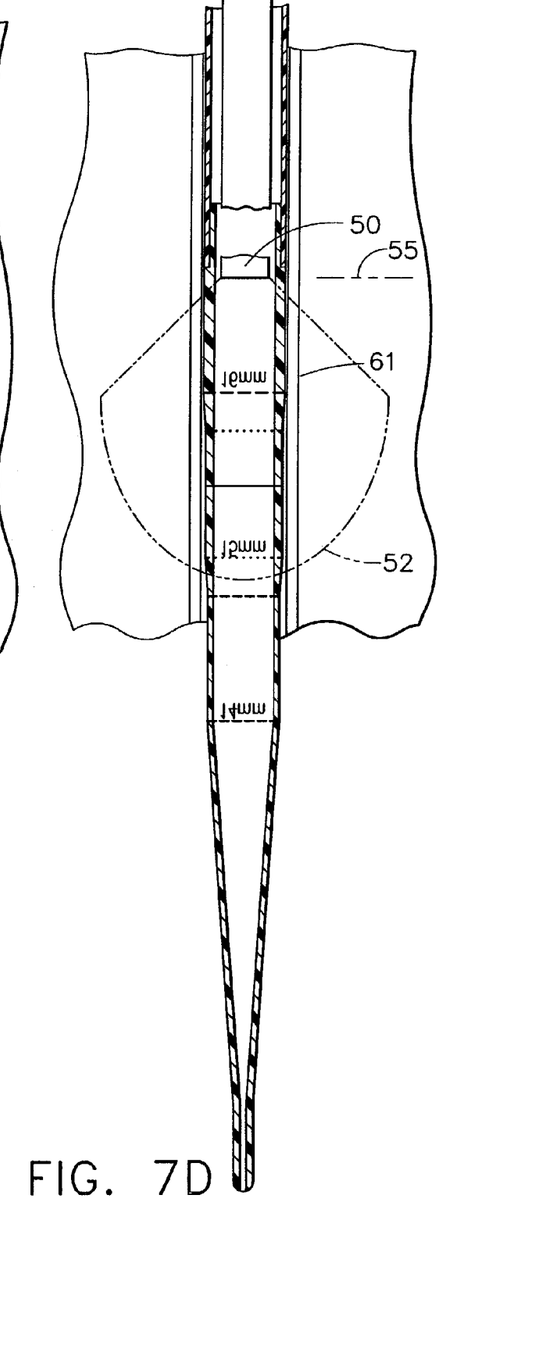

FIG. 7D shows endoscope 50 at a third viewpoint 55 so that field of view 52 includes third outer diameter D3. Again, the medical device may be further advanced to dilate stricture 61 to third outer diameter D3 while again viewing yet another portion of plurality of markings 43 as a reference. In this manner, the physician can visually examine the entire length of a stricture with endoscope 50 as the dilation occurs.

An alternative method of use is to first place a guidewire in body lumen 60 of the patient, then thread dilator 18 over that guidewire using second channel 27, conical inner contour 32, and first channel 23. Dilator 18 may then slide into the guidewire, after which endoscope 50 may be placed into first channel 23. The guidewire does not need to be threaded through the working channel of endoscope 50, but a physician may do so if desired. The combination of endoscope 50, dilator 18, and guidewire could then be used according to the steps illustrated in FIGS. 7A-7D.

A physician advancing a dilator through a stricture 61 will normally feel resistance. In prior art devices where the physician attempts to "blindly" introduce a dilator, perforation or other damage to the body lumen may occur. Further, if such damage occurs, the physician may not immediately recognize that damage has occurred. The present invention can permit the physician to visualize a medical procedure (e.g. dilation of a stricture) as the procedure is performed, thereby providing the physician with immediate feedback on the state of the tissue being treated. Such visualization can help in avoiding unintended damage of tissue which might otherwise occur if the physician is not able to directly visualize the procedure. In the unlikely even that damage does occur, the physician can immediately notice it and can choose to cease treatment and begin a new course of action to repair the damage. Direct visualization provided by endoscope 50 inside dilator 18 allows the physician to know that he/she has not perforated, bruised, or otherwise damaged body lumen 60.

Another useful feature of the dilator 18 is that it provides one with the ability to dilate to more than one diameter with a single introduction of the device, and with precision. This is made possible by the ability to see plurality of markings 43 from inside transparent segment 21 to identify a particular dilating diameter. Previously disclosed devices with multiple diameters rely on tactile feedback, remote markings, or costly pressure meters (e.g. in the case of balloons) to control the diameter. The intuitive nature of plurality of markings 43 allows the physician to easily select the desired diameter by looking clearly through the device, along the whole length of stricture 61, adding precision to the device when compared to current methods, which may involve elaborate measuring schemes.

Dilator 18 can also be less costly to manufacture than some balloon style dilators. Accordingly, devices of the present invention may be cost effectively packaged and sold as a single-use, disposable product which does not require cleaning or re-sterilization. Dilator 18 can be pre-sterilized and packaged in a sterile pouch or other suitable package.

Dilator 18 can also provide reliability in terms of dilating diameter compared to certain balloon type dilators. Some balloons may not hold a constant diameter when inflated, so the dilation is not as reproducible as a tube of known size being passed through a constricted area. Dilator 18 provides two-vector shearing of stricture 61. This results from sliding a tapered-tip device through a narrowed area, thereby applying forces in both the axial and radial directions. Balloons typically only apply a generally radial directed force to a stricture.

Dilator 18 can also provide affordable and convenient dilation with the ability to directly visualize the treatment along the entire length (not just a proximal or distal portion) of a stricture 61 without the use of expensive or potentially harmful radiographic equipment to confirm placement. When using radiographic equipment, a dilation procedure is typically performed in a radiographic suite, which often requires additional logistics of scheduling an additional appointment and different staffing needs, which in turn can require additional time and cost. Dilator 18 can provide complete direct visualization with endoscope 50 without the additional costs or time associated with radiographic equipment.

The present invention has been illustrated as having a transparent segment having generally circular cross-sections, but non-circular cross-sections (e.g. oval, elliptical, polygonal) can also be used, in which case the term "diameter" will be understood to refer to the maximum dimension of the non-circular cross-section used for providing dilation. The present invention may be provided in kit form with other medical devices, and the kit elements can be pre-sterilized and packaged in a sealed container or envelope to prevent contamination. The present invention may be provided as single use disposable device or alternatively, may be constructed for multiple uses.

While various embodiments of the present invention have been disclosed, it will be obvious to those skilled in the art that such embodiments are provided by way of example only. Further, each element or component of the present invention may be alternatively described as a means for performing the function or functions performed by the element or component. Numerous variations, changes, and substitutions will now occur to those skilled in the art without departing from the invention. Accordingly, it is intended that the invention be limited only by the spirit and scope of the appended claims.

What is claimed is:

1. A medical device for use with an endoscope in dilating a body lumen, the medical device comprising a generally transparent segment having:
    a distal tapered tip having a guidewire passageway extending therethrough;
    a first cylindrical section having an axial length, the first cylindrical section disposed proximally of the distal tapered tip and disposed distally of a first tapered transition portion, the first cylindrical section having a substantially constant first outer diameter sized for providing dilation of a body lumen, and a first channel extending at least partially into said first cylindrical section, wherein the channel has an internal diameter larger than that of the guidewire passageway and wherein the channel is sized for receiving an endoscope,
    a second cylindrical section disposed proximally of the first tapered transition portion and disposed distally of a second tapered transition, the second cylindrical section having a substantially constant second outer diameter sized for providing dilation of a body lumen, wherein said second outer diameter is larger than said first outer diameter, and
    a third cylindrical section disposed proximally of the second tapered transition portion, the third cylindrical section having a substantially constant third outer diameter sized for providing dilation of a body lumen, wherein said third outer diameter is larger than said second outer diameter,
    wherein each of the first, second, and third outer diameters is provided without inflation of the generally transparent segment.

2. The medical device of claim 1 further comprising a plurality of markings on said transparent segment, wherein said plurality of markings are viewable with an endoscope positioned in said channel.

3. The medical device of claim 2 wherein said plurality of markings delineates the portion of said transparent segment having said first outer diameter.

4. The medical device of claim 2 wherein said plurality of markings indicates the numeric value of said first outer diameter.

5. The medical device of claim 1 wherein the distal tapered up has an axial length greater than the axial length of the first cylindrical section.

6. The medical device of claim 1 further comprising a coating for reducing friction, wherein said coating is generally transparent.

7. The medical device of claim 6 wherein said coating is located on the inner surface of said transparent segment.

8. The medical device of claim 6 wherein said coating is located on the outer surface of said transparent segment.

9. The medical device of claim 1 further comprising a handle positioned proximally of said transparent segment, wherein said handle includes a longitudinal channel in communication with said first channel for receiving the endoscope.

10. A medical device for use with an endoscope, comprising:
    (a) a tube comprising a first channel for receiving the endoscope;
    (b) a unitary, transparent segment extending distally of said tube, said transparent segment for dilating a body lumen, said transparent segment having a first cylindrical outer surface having a substantially constant first outer diameter, a second cylindrical outer surface having substantially constant second outer diameter larger than the first diameter, and a third cylindrical outer surface having a substantially constant third outer diameter larger than the second diameter, said diameters arranged to provide sequential dilation, wherein the transparent segment is configured to provide sequential dilation at each of the first, second, and third outer diameters in the absence of a pressurized fluid within the transparent segment;
    (c) a plurality of markings visible with an endoscope disposed in said first channel, wherein said plurality of markings delineate portions of said transparent segment having said first outer diameter, said second outer diameter, and said third outer diameter; and
    (d) a tapered tip extending distally of said first cylindrical outer surface.

* * * * *